United States Patent
Sander et al.

(10) Patent No.: US 7,875,063 B1
(45) Date of Patent: *Jan. 25, 2011

(54) TISSUE REPAIR DEVICE AND APPARATUS AND METHOD FOR FABRICATING SAME

(75) Inventors: Thomas W. Sander, Winona Lake, IN (US); Daniel R. Lee, Madison, CT (US); Wayne C Person, Newton, CT (US); Steven Howansky, Wilton, CT (US)

(73) Assignee: Tyco Healthcare Group LP, North Haven, CT (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/369,858

(22) Filed: Jan. 6, 1995

Related U.S. Application Data

(63) Continuation of application No. 08/144,453, filed on Oct. 27, 1993, now abandoned, which is a continuation-in-part of application No. 07/699,991, filed on May 13, 1991, now Pat. No. 5,269,783.

(51) Int. Cl.
   *A61B 17/04* (2006.01)
(52) U.S. Cl. .................. 606/300; 606/77; 606/138; 606/228
(58) Field of Classification Search ............ 606/72–78, 606/224–228, 233, 60, 139, 222, 223, 230, 606/232, 139.142, 216, 219, 300; 264/4, 264/78, 37.27, 225, 319, 320, 327, 496, 642
See application file for complete search history.

(56) References Cited

U.S. PATENT DOCUMENTS

| | | | | | |
|---|---|---|---|---|---|
| 2,075,508 | A | * | 3/1937 | Davidson | 606/232 |
| 2,199,025 | A | * | 4/1940 | Conn | 606/232 |
| 2,802,468 | A | * | 8/1957 | Everett | 606/226 |
| 3,123,077 | A | * | 3/1964 | Alcamo | 606/228 |
| 3,570,497 | A | | 3/1971 | Lemole | |
| 3,728,839 | A | * | 4/1973 | Glick | 53/425 |
| 3,875,946 | A | | 4/1975 | Duncan | |
| 3,890,975 | A | | 6/1975 | McGregor | |
| 3,905,376 | A | * | 9/1975 | Johnson et al. | 36/154 |
| 3,945,786 | A | * | 3/1976 | Bishop | 425/208 |
| 3,976,079 | A | * | 8/1976 | Samuels et al. | 606/232 |

(Continued)

FOREIGN PATENT DOCUMENTS

EP 0314412 * 5/1989 .................. 606/228

(Continued)

OTHER PUBLICATIONS

Ethicon Brochure, 1966 4 Pages.*

(Continued)

*Primary Examiner*—Michael A. Brown

(57) ABSTRACT

A method for fabricating a device for repairing torn tissue or muscle such as the meniscus of the knee. The device includes a pair of anchoring members having a plurality of barb-like projections extending outwardly therefrom. The anchoring members are joined by a flexible linking member which connects the ends of the anchoring members opposite one another. Such a device can be fabricated by insert molding of the appropriate members together.

26 Claims, 13 Drawing Sheets

U.S. PATENT DOCUMENTS

| | | | | |
|---|---|---|---|---|
| 3,981,307 | A | * | 9/1976 | Borysko .................. 606/224 X |
| 4,344,193 | A | | 8/1982 | Kenny |
| 4,359,053 | A | * | 11/1982 | Benjamin .................... 606/226 |
| 4,399,093 | A | * | 8/1983 | Kirby et al. .............. 264/328.2 |
| 4,490,326 | A | | 12/1984 | Beroff et al. |
| 4,492,577 | A | * | 1/1985 | Farris et al. .............. 433/201.1 |
| 4,510,934 | A | * | 4/1985 | Batra ......................... 606/231 |
| 4,523,591 | A | | 6/1985 | Kaplan et al. |
| 4,549,545 | A | * | 10/1985 | Levy .......................... 606/228 |
| 4,635,637 | A | | 1/1987 | Schreiber |
| 4,649,920 | A | * | 3/1987 | Rhum ........................ 606/230 |
| 4,696,300 | A | | 9/1987 | Anderson |
| 4,712,550 | A | | 12/1987 | Sinnett |
| 4,741,330 | A | | 5/1988 | Hayhurst |
| 4,743,257 | A | | 5/1988 | Tormala et al. |
| 4,744,365 | A | | 5/1988 | Kaplan et al. |
| 4,781,190 | A | | 11/1988 | Lee |
| 4,784,285 | A | * | 11/1988 | Patel .......................... 220/782 |
| 4,786,454 | A | | 11/1988 | Oddenino |
| 4,790,303 | A | * | 12/1988 | Steffee ........................ 606/61 |
| 4,822,434 | A | * | 4/1989 | Sawaki et al. ................. 156/48 |
| 4,858,603 | A | | 8/1989 | Clemow |
| 4,869,242 | A | | 9/1989 | Galluzzo |
| 4,873,976 | A | | 10/1989 | Schreiber |
| 4,875,479 | A | * | 10/1989 | Belykh et al. ............... 606/230 |
| 4,885,121 | A | * | 12/1989 | Patel .......................... 264/255 |
| 4,895,148 | A | | 1/1990 | Bays et al. |
| 4,901,712 | A | | 2/1990 | Voegell et al. |
| 4,922,904 | A | * | 5/1990 | Uetake ....................... 606/226 |
| 4,926,860 | A | | 5/1990 | Stice et al. |
| 4,932,962 | A | * | 6/1990 | Yoon .......................... 606/224 |
| 4,950,285 | A | * | 8/1990 | Wilk ....................... 606/151 X |
| 4,976,715 | A | | 12/1990 | Bays et al. |
| 4,981,149 | A | * | 1/1991 | Yoon et al. .................. 128/898 |
| 4,990,158 | A | | 2/1991 | Kaplan et al. |
| 4,997,436 | A | | 3/1991 | Oberlander |
| 5,002,562 | A | * | 3/1991 | Oberlander ................. 606/221 |
| 5,019,093 | A | | 5/1991 | Kaplan et al. |
| 5,053,047 | A | | 10/1991 | Yoon |
| 5,059,206 | A | | 10/1991 | Winters |
| 5,074,874 | A | * | 12/1991 | Yoon .......................... 606/224 |
| 5,080,667 | A | * | 1/1992 | Chen .......................... 606/225 |
| 5,089,012 | A | * | 2/1992 | Prou .......................... 606/224 |
| 5,102,421 | A | | 4/1992 | Anspach, Jr. |
| 5,133,738 | A | | 7/1992 | Korthoff et al. |
| 5,147,400 | A | | 9/1992 | Kaplan et al. |
| 5,154,189 | A | | 10/1992 | Oberlander |
| 5,163,960 | A | * | 11/1992 | Bonutti ...................... 128/898 |
| 5,181,923 | A | | 1/1993 | Chesterfield et al. |
| 5,226,912 | A | * | 7/1993 | Kaplan et al. ............... 606/224 |
| 5,280,674 | A | * | 1/1994 | Granger ..................... 606/224 |
| 2008/0131544 | A1 | * | 6/2008 | Sander et al. ............... 425/116 |

FOREIGN PATENT DOCUMENTS

| | | | |
|---|---|---|---|
| EP | 0390613 | | 10/1990 |
| EP | 0 513 736 | | 11/1992 |
| GB | 1 506 362 | | 4/1978 |
| GB | 2 192 362 | | 1/1988 |
| WO | 3396 | * 6/1986 | .................. 606/224 |
| WO | 8701270 | | 3/1987 |

OTHER PUBLICATIONS

Encyclopedia of Chemical Technology, vol. 18 (3rd Ed.) p. 195-199.
Encyclopedia of Polymer Science and Engineering, vol. 8 (2nd Ed.) p. 102-138.
Thermoplastic: Effects of Processing (1969) p. 110-182.
Encyclopedia of Polymer Science and Engineering, Supplemental Volume (2nd Ed.) p. 507-509.
A brochure entitled "The Meniscal Anchor" from GMI, Inc.
"A Needle Guided Resorbable Staple For Arthroscopic Meniscal Repair" by Daniel F. Justin.
"A Technique of Arthroscopic Meniscoplasty" by Vincent J. DiStefano, MD and Paul Bizzle, DO.
"Arthroscopic Meniscal Repair" by William G. Clancy, Jr., MD and Ben K. Graf, MD.
"Arthroscopic Repair of Meniscus Tear" by Charles E. Henning, MD.
US 5,035,707, 07/1991, Korthoff (withdrawn)*

* cited by examiner

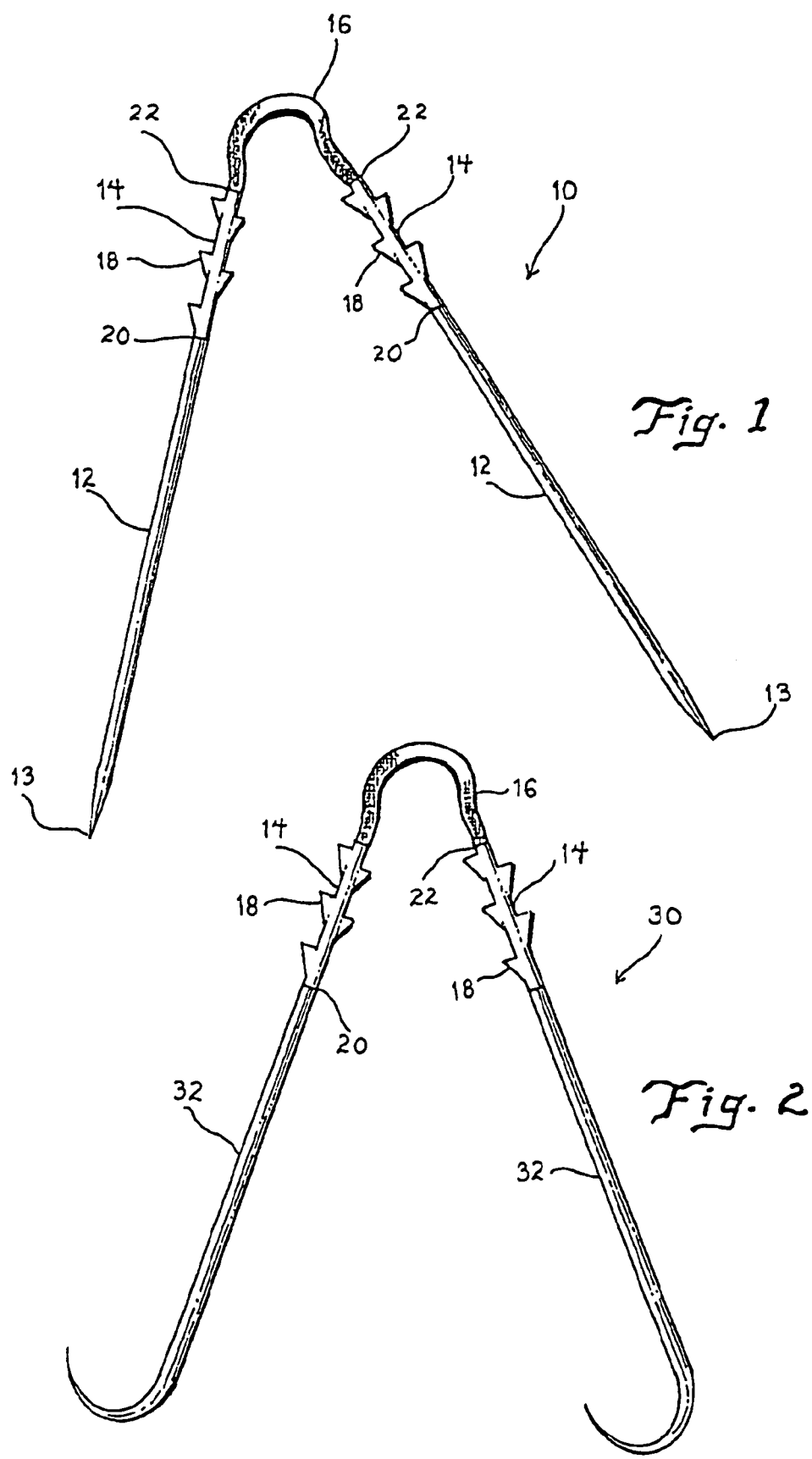

TISSUE REPAIR DEVICE AND APPARATUS AND METHOD FOR FABRICATING SAME

CROSS REFERENCE TO RELATED APPLICATION

This is a continuation of application Ser. No. 08/144,453, filed on Oct. 27, 1993 now abandoned, which is a continuation-in-part of Ser. No. 07/699,991, filed May 13, 1991 now issued as U.S. Pat. No. 5,269,783.

BACKGROUND OF THE INVENTION

1. Field of the Invention

The present invention relates to a device for repairing torn tissue and muscle in the body, and more particularly to a device for repairing a torn meniscus in the human knee. A method of repairing torn meniscal tissue is also disclosed. The present invention is also directed to apparatus and method for fabricating the invention device.

2. Discussion of the Prior Art

The surgical repair of torn tissue and muscles in the body has typically been performed through incisions in the body to expose the area under repair and the actual procedure includes the provision of sutures, staples or fasteners. The advent of arthroscopic techniques and endoscopic equipment have reduced the size and depth of the incision required to perform the repair procedure. However, the use of conventional devices in many cases requires a highly skilled surgeon to perform the repair, and usually requires complete immobilization of the surgical area following the repair procedure.

Surgical repair of cartilage and muscle in joints such as the knee often requires extraordinary skill on the part of the surgeon to reduce damage to adjacent nerves, blood vessels, muscles and tendons in the knee joint. In particular, surgical repair of the fibrocartilage disks within the knee known as the menisci, which are attached peripherally to the joint capsule, requires precision to avoid such damage.

In the past, meniscal surgery has included procedures for partial to complete removal of a torn meniscus, as well as attempts to surgically suture, staple or tack the tear in the meniscus to allow for healing. Other techniques have included removal of portions of the meniscus to arrest the spread of the tear.

A technique has been developed using arthroscopic instruments which provides for meniscal repair through the use of a pair of surgical needles which are inserted through cannuli into the knee on opposite sides of the tear in the meniscus to be repaired. The needles are linked by a single suture which is pushed down through the cannuli and across the tear. An incision is made in the skin at the point where the needles exit the knee joint so that the leading end of each needle may be grasped and pulled through the joint. The ends of the sutures are then grasped after the needles are removed from the suture ends and the suture is then tied outside the skin so that a horizontal suture is created in the meniscus. This procedure is repeated for placement of as many sutures as necessary to repair the meniscus tear. This process is very time consuming, and the strength of the repair is dependent upon the tension created by the knot tied in the suture.

The need exists for a device for repairing torn tissue, such as the meniscus of the knee, which obviates the disadvantages encountered in the prior art and provides an efficient, suture-type device which expedites the surgical procedure and reduces the amount of precision necessary on the part of the surgeon during the procedure. Additionally, there is a need for providing smooth, reliable fabrication of a suture-type device for repairing torn tissue such as the knee meniscus, especially for fabricating such a device out of material having dissimilar flexibilities.

In this regard, two general processing techniques have been previously utilized for attaching a fiber or filamentous structure such as a braid to a solid object. The first such general process involved the mechanical crimping or tying of the braid to a solid piece. The second technique involved welding the braid to the solid piece by using energy such as heat, ultrasound, etc. or chemicals such as solvent, glue or adhesive, etc. However, these prior techniques are either extremely cumbersome or fail to form reliable, secure attachment between materials of dissimilar flexibilities. Accordingly, the need exists for smooth, reliable fabrication of such tissue repair devices, notably surgical implants prepared from resorbable materials such as surgical clips or staples.

SUMMARY OF THE INVENTION

The present invention provides a novel device for repairing torn tissue and muscle such as the menisci in the knee joint which expedites the surgical process and facilitates complete healing of the tear. The device of the present invention reduces the precision required on the part of the surgeon to accurately place and secure the suture at the tear site, and expedites the surgical process by eliminating the requirement of securing the ends of the sutures together to stitch the tear. The device of the present invention allows a surgeon to reduce the trauma to the surrounding tissue and facilitates healing of the torn muscle tissue by providing a completely resorbable suture-like device which may be accurately placed across the tear and which may remain in place until the tear is completely healed.

The device for repairing torn tissue and muscles of the present invention comprises a pair of surgical needles each secured at one end to a pair of anchoring members which essentially comprise absorbable rods having outwardly projecting barbs. Each anchoring member is secured at a second end to an absorbable flexible material such as a suture which extends between the two anchoring members. The means of securement between the needles and anchoring members, and between the anchoring members and the suture may include adhesives, swaging, crimping or a quick-release connection such as heat-shrinkable tubing. Preferably, the suture and the anchoring members are constructed of a bioresorbable material.

The barbs of the anchoring member have a tapered configuration towards the needles so that as the needles are pushed through the tissue, the barbs easily pass through the tissue with the needle. The configuration of the barbs is such that the anchoring members pass easily through the tissue in the forward direction, but are prevented from moving in the reverse direction. The barbs are provided to anchor the device in the tissue.

The needles of the present invention may be straight needles, preferably constructed of stainless steel or other surgical grade metal alloy. Although preferably straight, it is contemplated that the needles may be curved, similar to suture-type needles.

In use, the damaged or torn meniscus in the knee is arthroscopically approached from the front of the knee by inserting the needles across the tear and then advancing the needles through the meniscus across the tear, drawing the absorbable anchoring means through the meniscus and then through the joint capsule to exit through a previously made incision. The suture is then pulled substantially flush with the meniscus across the tear, whereby the surgeon may then pull the needles through the incision, which had been made to expose the outer surface of the joint capsule. The needles are then cut, or may be detached by a sharp pull when the suture contacts the meniscus across the tear. The barbed anchoring means are then cut substantially flush with the joint capsule on the side opposite the suture, the incision is closed; and the anchoring means holds the suture in place. The barbs on the anchoring means serve to maintain the position of the device within the meniscus, and the suture and anchoring means serve to maintain the tear at close approximation to enhance healing. The material compositions of the suture and the anchoring means are selected to provide the desired resorption rate to allow sufficient time for healing.

In the event that the tissue being repaired is not sufficiently strong to retain the barb members in place, a retaining flange may be utilized which is slipped over the barbs after it is drawn through the tissue to apply counter pressure against the surface of the joint capsule to pull the suture tight across the tear.

The present invention is also directed to apparatus and method for fabricating the repair device supra which are effective for joining elements formed of materials having dissimilar flexibilities to provide a device that will effectively function when used to repair torn tissue. In particular, the invention apparatus and method can be used to fabricate a series of tissue repair devices at one time.

In the fabrication of a composite device of materials having dissimilar flexibilities in accordance with the invention, one of the pieces of material, e.g., the material of greater flexibility, is first placed in a mold such as a compression or injection mold. The material of different flexibility, e.g., polymeric material of less flexibility, is then injection or compression molded about the material previously placed in the mold cavity. When forming a meniscal staple, a segment of braided suture material which can be resorbable is placed within a channel or groove of the mold that interconnects cavities for molding the substantially rigid tips. Into each rigid tip cavity, a portion of the length of braided suture material passes and is positioned so that the braided suture material is centrally located within the respective cavities. The mold halves are then closed and the molding polymer is introduced into the cavities, e.g., by injection. The molten or flowable polymer then surrounds and encapsulates the braided suture material extending into the rigid tip cavities. Upon cooling of the molten material, a composite meniscal staple device is formed from materials having dissimilar flexibilities where the braided suture is firmly attached to the molded rigid tips of the staple.

The present invention provides for facilitated attaching of a flexible member, e.g., a braided suture, to a rigid part, notably where both flexible and rigid members are fabricated from resorbable material as in the case of forming surgical implants. A composite member which can be used as a tissue repair device is thereby fabricated and possesses secure attachment between materials of dissimilar flexibilities, e.g., a uniquely shaped, rigid, hard solid component reliably coupled to a flexible yet tensilely strong fibrous or filamentous structure.

BRIEF DESCRIPTION OF THE DRAWINGS

The foregoing features of the present invention will become more readily apparent and may be understood by referring to the following detailed description of illustrative embodiments of the device for repairing torn tissue and muscle and apparatus and method for fabricating the same taken in conjunction with the accompanying drawings, in which:

FIG. 1 illustrates a perspective view of the device of the present invention;

FIG. 2 illustrates a perspective view of an alternate embodiment of the device of the present invention;

DETAILED DESCRIPTION OF THE PREFERRED EMBODIMENTS

Figure 3:
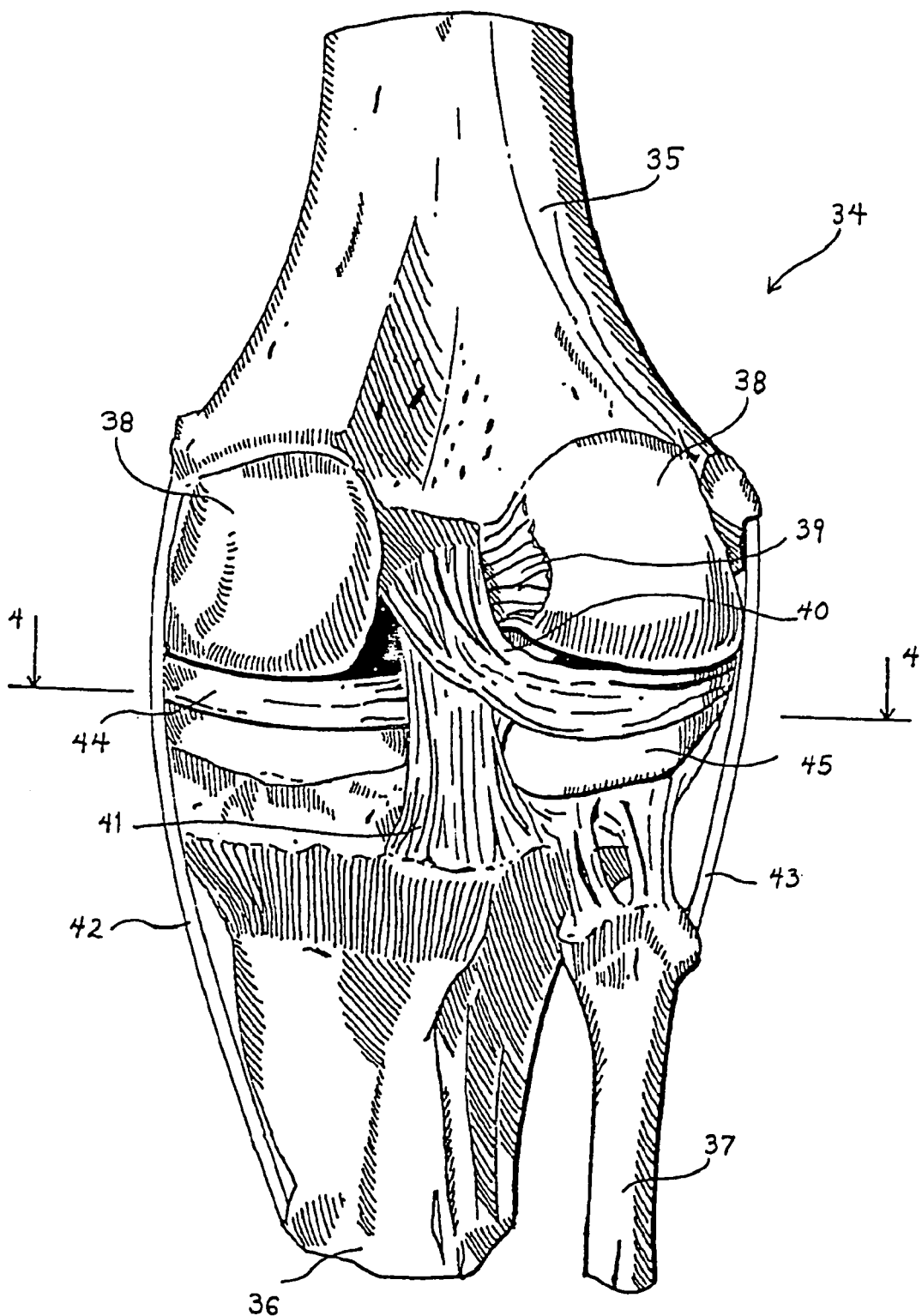
FIG. 3 illustrates a perspective posterior view of the muscular structure of the knee.

Referring now in specific detail to the drawings, in which like reference numerals identify similar or identical elements throughout the several views, FIG. 1 shows the repair device 10 of the present invention. Repair device 10 generally comprises a pair of metal needles 12, preferably constructed of stainless steel or other surgical metal alloy, having a sharp tip 13 at one end to facilitate penetration through tissue, and a blunt end at the other end. In a preferred embodiment, the length of each needle is between 6 inches and 10 inches. However, this is not intended to be limiting as clearly needles of various lengths may be utilized.

Secured to needles 12 are a pair of anchoring members 14 which are constructed of a bioresorbable material, such as homopolymers and copolymers of lactide, glycolide, polydioxanone, trimethylene carbonate, polyethylene oxide or other bioabsorbable materials or blends of these copolymers. Preferably, the anchoring members 14 are formed of a copolymer of lactide and glycolide. Anchoring members 14 are linked by a flexible material 16 such as a suture, also constructed of a bioresorbable material, such as a lactide/glycolide copolymer. Flexible material 16 allows for movement of anchoring members 14 with respect to one another. Anchoring members 14 preferably have a length of between about 0.040 inch and 2 inches, more preferably between about 0.050 inch and one inch.

Needles 12 are secured to anchoring members 14 as indicated at joint 20, and the anchor members 14 are secured to suture 16 as at joint 22. The anchoring members 14 of device 10 may be secured to the needles 12 by means of adhesives, crimping, swaging or the like, and joint 20 may be formed by heat-shrinkable tubing. It is preferred that joint 20 is a detachable connection, such that needle 12 may be removed from anchoring member 14 by a sharp tug or pull or by cutting as described below. Anchoring members 14 are secured to suture 16 preferably by insert molding.

Anchoring members 14 are provided with a plurality of barb-like projections 18 which serve to anchor device 10 in the tissue to be repaired. Barbs 18 have a tapered shape to allow the anchoring members 14 to be pushed through tissue or muscle, such as the menisci of the knee, in a first forward direction and to prevent the anchor members from traveling in a reverse direction. Although as shown in FIG. 1 five barbs 18 are provided, any number may be provided, so long as the barbs penetrate the tissue to anchor the device 10.

FIG. 2 illustrates an alternate embodiment of the device of the FIG. 1. Device 30 is similar in construction to device 10 except that curved needles 32 are provided. Needles 32 are secured to anchoring members 14 as described above, which are provided with a plurality of barbs 18 which taper in the direction of needles 32 to facilitate insertion of the device into tissue. Anchoring members 14 are connected through suture 16 as described above. The remaining elements of device 30 are identical to those of device 10 as illustrated in FIG. 1.

FIG. 3 illustrates the muscular and ligament structure of the knee 34, including the pertinent components of the knee to which the present invention is directed. As is well known, the femur 35 is joined to tibia 36 and fibula 37 by muscles, tendons and ligaments, and these bones are separated and cushioned by the medial meniscus 44 and lateral meniscus 45. Condyles 38 of femur 35 rest on the menisci, and the bones are joined and supported by anterior cruciate ligament 39, ligament of Wrisberg 40, posterior cruciate ligament 41, and transverse ligament 46 (see FIG. 5). The joint capsule is formed by tibial collateral ligament 42 and fibular collateral ligament 43.

Figure 4:
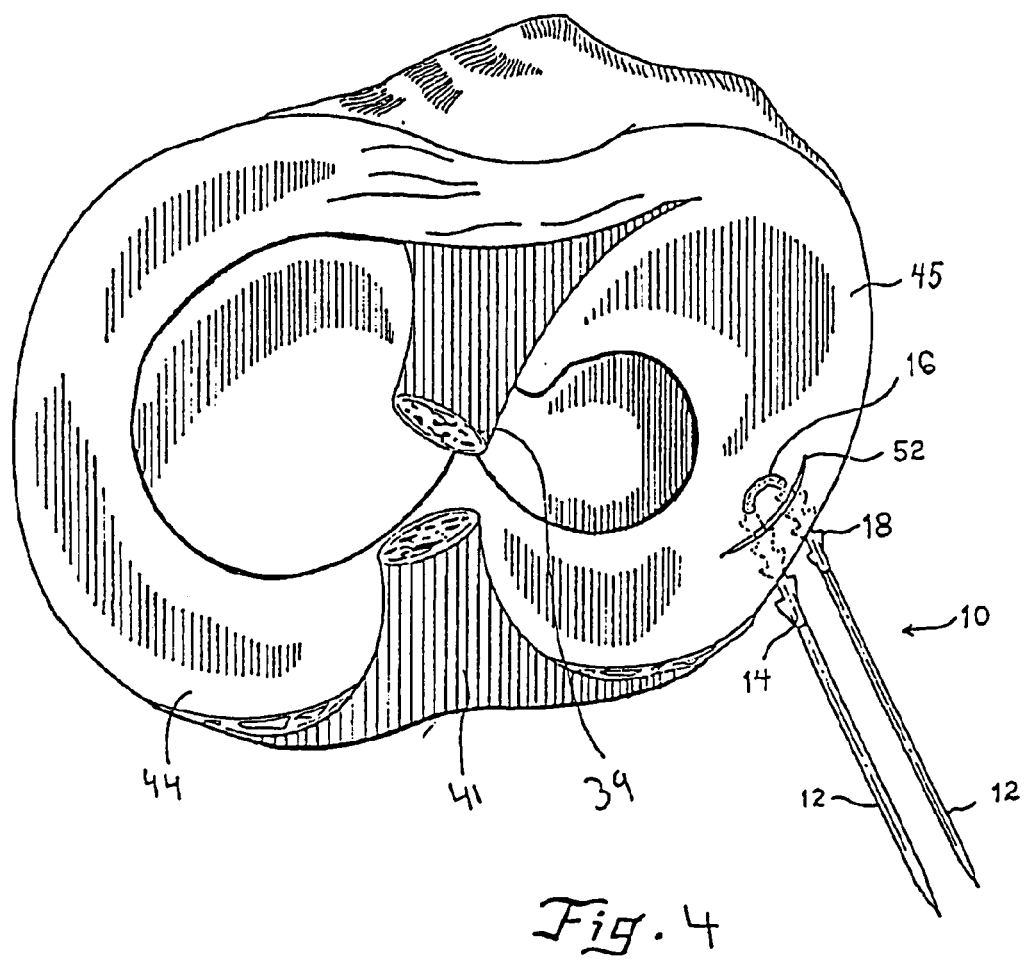
FIG. 4 illustrates a cut-away perspective view of the knee of FIG. 3 along line 4—4 showing the device of the present invention in position during the meniscal repair procedure.

FIG. 4 illustrates the device 10 of the present invention in use, showing knee 34 along lines 4—4 of FIG. 3. The lateral meniscus 45 of a knee 34 having a tear 52 is repaired with the present invention by forcing needles 12 through the meniscus on one side of the tear, through the torn region, and out the meniscus tissue on the opposite side of the tear on the outside of the knee. The device is fully inserted so that flexible member 16 becomes substantially flush with meniscus 45 and is pulled taut. Barbs 18 of anchoring members 14 anchor the device in the meniscus 45 and prevent the device from backing off, so that tear 52 is maintained in an abutting relationship across itself to facilitate healing. Needles 12 may then be removed from anchoring members 14 by means of a sharp yank or tug, or are cut as they are accessed from the opposite side of the knee by a suitable incision. Anchoring members 14 are then trimmed so as to be flush with the surface of meniscus 45 or the joint capsule. The material of which anchoring members 14 and suture 16 are constructed are preferably bio-resorbable materials which resorb at a rate which is slow enough to facilitate healing of the tear in the tissue.

Figure 5:
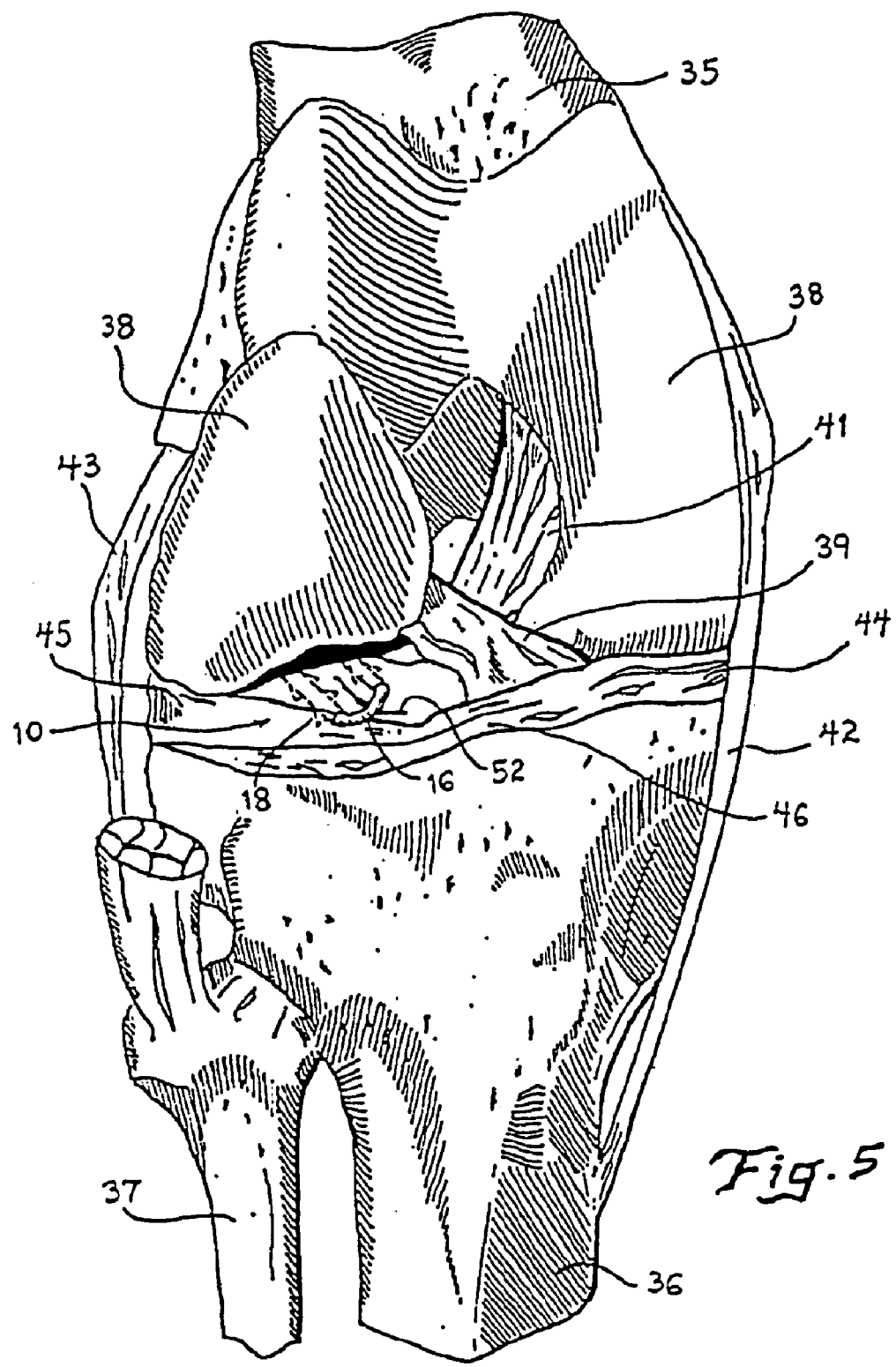
FIG. 5 illustrates a perspective anterior view of the knee of FIG. 3 with the device of the present invention in position during the meniscal repair procedure.

During arthroscopic surgery, as best seen in FIG. 5, the surgeon will approach the torn meniscus from in front of the knee and insert the two needles 12 into the meniscus 44 or 45. As the needles 12 are pushed through the meniscus 45 to draw the edges of the tear together, the surgeon will make an incision on the opposite side of the knee adjacent the needles to avoid pushing the needles through the skin. As the needles are withdrawn, the suture 16 is pulled tight to hold the edges of the tear together while the barbs 18 prevent the backing off of the device 10 through the tissue. The needles are then removed, and the anchor members are trimmed to the surface level of the joint capsule and the incisions are stitched.

Figure 6:
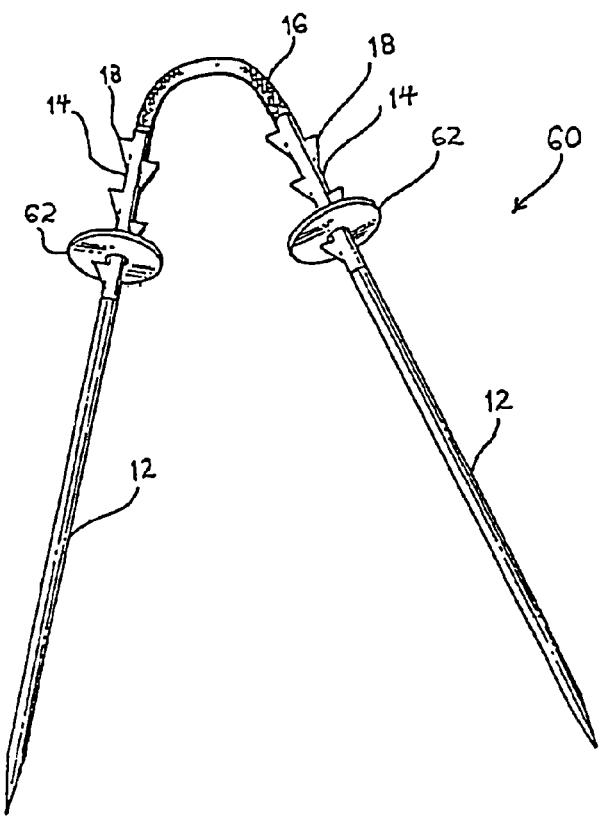
FIG. 6 illustrates a perspective view of an alternate embodiment of the device of FIG. 1.

Turning now to FIG. 6, there is shown a further embodiment of the device of the present invention. Device 60 is identical to device 10 except for the provision of retaining flanges 62 which slip over needles 12 and anchoring members 14 to apply counter pressure against the surface of the joint capsule to pull the suture 16 tight across the tear in the meniscus. Flanges 62 are utilized when the strength of the tissue through which the device passes is insufficient to hold barbs 18 in place.

Figure 7:
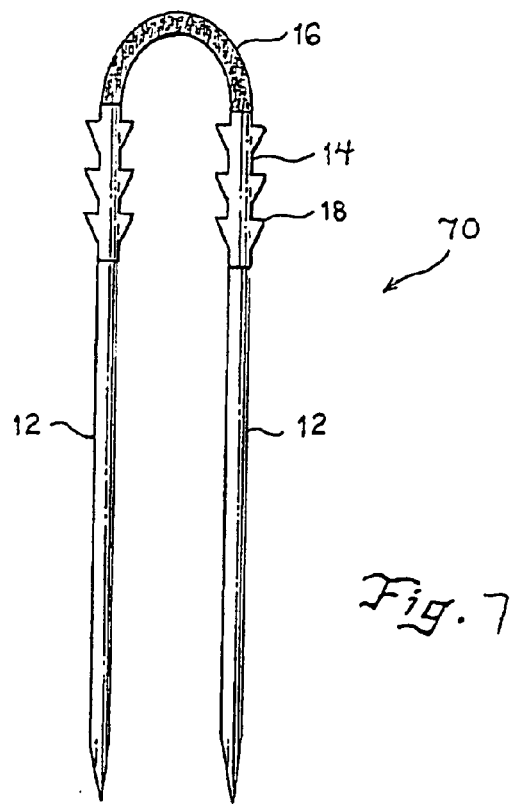
FIG. 7 illustrates a perspective view of a further alternate embodiment of the device of FIG. 1.

FIG. 7 illustrates a further embodiment of the device of the present invention. Device 70 is identical to device 10 except that barbs 18 are aligned with each other, rather than staggered as in accordance with FIG. 1. Clearly, device 70 may include curved needles as shown in FIG. 2 or retaining flanges 62 as shown in FIG. 6.

As noted supra, anchoring members 14 are preferably secured to suture 16 by insert molding. The techniques of compression and injection molding are per se well-known. For example, injection molding is described, e.g., by Paul N. Richardson, "Plastics Processing", *Encyclopedia of Chemical Technology, Volume* 18 (Third Edition), John Wiley & Sons, pp. 195–199; Irvin N. Rubin, "Injection Molding", *Encyclopedia of Polymer Science and Engineering, Volume* 8 (Second Edition) John Wiley & Sons, pp. 102–138; and A. B. Glanvill, "Injection Moulding", *Thermoplastics: Effects of Processing*, London Iliffe Books Ltd., 1969, pp. 110–182. More specifically, the injection molding process involves heating thermoplastic material so that such material is rendered in flowable condition. After the thermoplastic material has been rendered sufficiently molten, the material is then injected into the mold cavity defined between the mold and counter mold portions, e.g., by a piston head or extruder screw. Compression molding is described, e.g., by Herbert Rees, "Mold", *Encyclopedia of Polymer Science and Engineering, Supplemental Volume* (Second Edition), John Wiley & Sons, pp. 507–509, which also describes injection molding and a combination of injection-compression molding.

Using the technique of compression molding, the material retaining its initial form, e.g., a flexible braided suture, is first placed in an open mold, followed by introduction of an excess of molten thermoplastic material. The mold is then closed with the mold halves compressed together to shape the molten material as it hardens and forms rigid members attached to, e.g., the flexible braid. In this respect, using an excess of thermoplastic material together with proper application of heat and pressure in a compression mold allows the material to flow within the mold cavity and then solidify to form rigid members of proper dimensions. A heating/cooling pipe and/or other heating/cooling sources can be provided within the mold portions to control heat application and prevent damage or changes to the braid structure.

Figure 8:
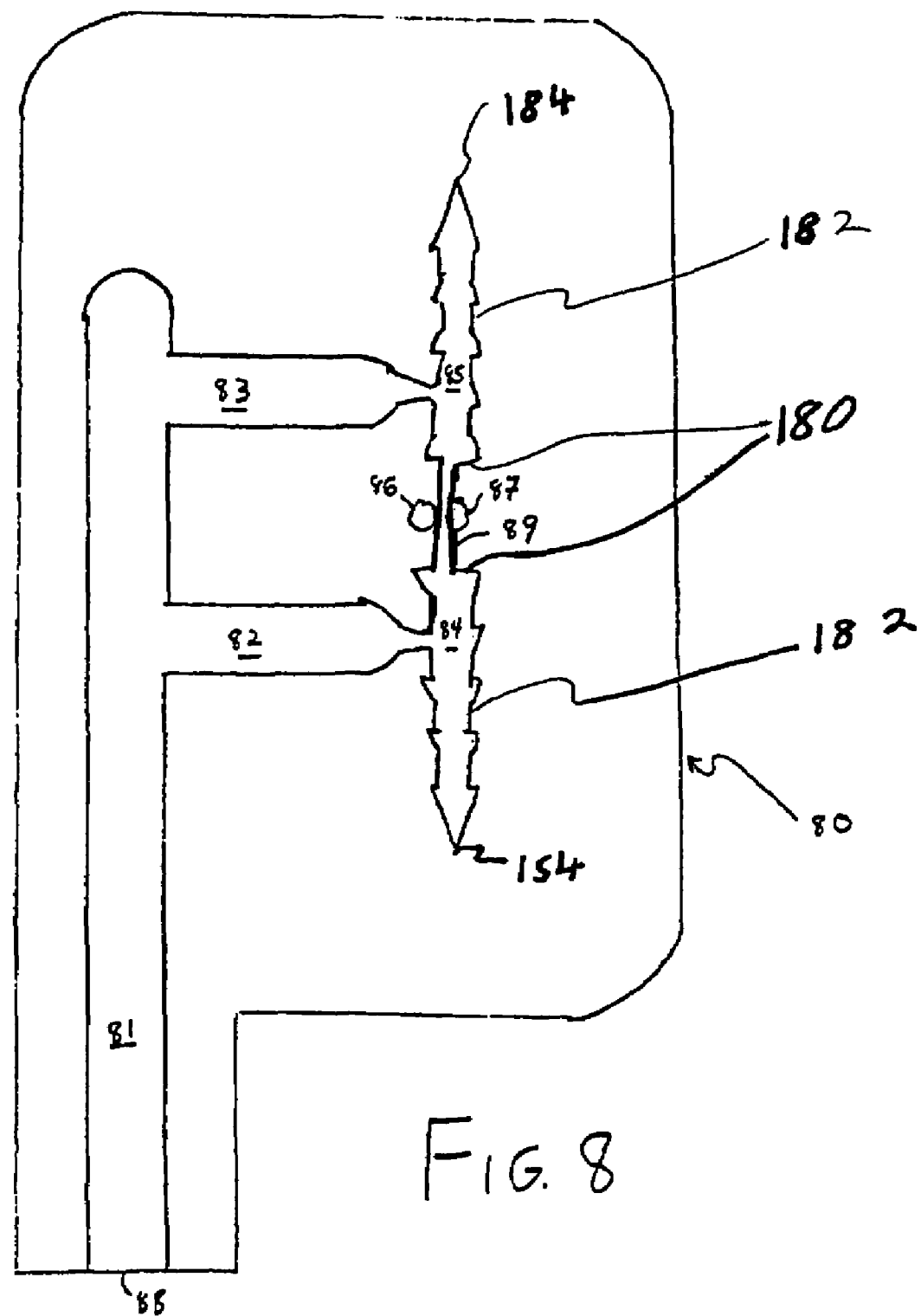
FIG. 8 is a top plan view of a portion of apparatus for fabricating the device of the present invention.
Figure 9:
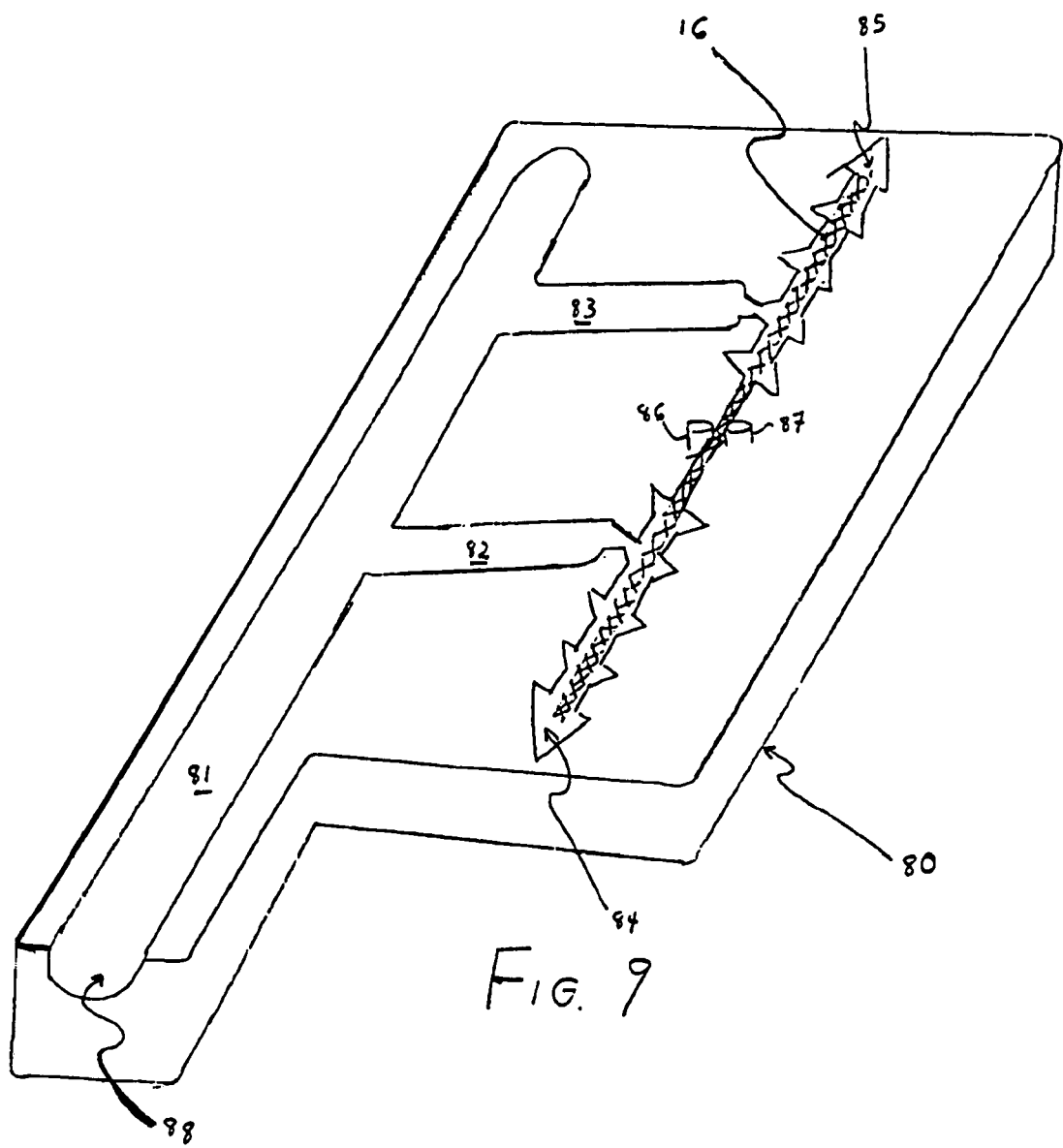
FIGS. 9 and 10 are a schematic perspective views of the apparatus portion shown in FIG. 8 illustrating steps in the fabrication of the invention device.
Figure 10:
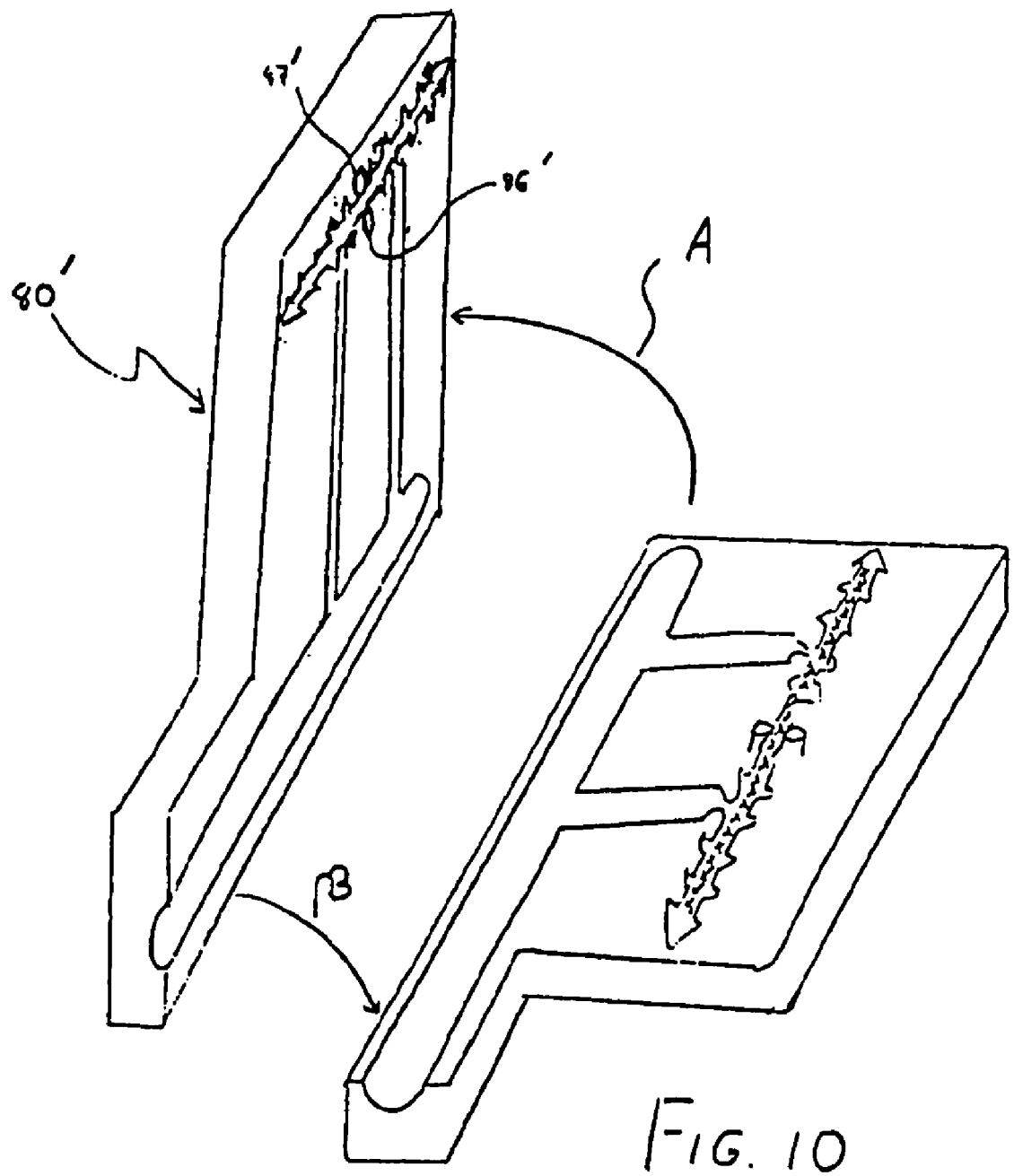

In this regard, compression or injection molding apparatus is provided as part of the present invention for joining the suture 16 and anchoring members 14. An embodiment of such apparatus is illustrated in FIGS. 8–10. More particularly, FIG. 8 illustrates a mold portion 80 forming part of the injection molding apparatus, this mold portion 80 comprises various tracks or recesses 81–85, including inlet channel 81, and projecting pegs 86 and 87. A countermold portion 80' (FIG. 10) is formed as an exact mirror image to mold portion 80, the only difference being that recesses 86', 87' are provided in the countermold portion 80' at the location corresponding to projecting pegs 86 and 87 in mold portion 80. Projecting pegs 86 and 87 are positioned to mate with the corresponding recesses 86' and 87' in the countermold portion 80' when the mold portion 80 and countermold portion 80' are secured together, thereby defining internal channels or cavities along recesses 81–85 which are entirely enclosed except for the open end 88 of recess 81. Additional pegs and corresponding recesses can be provided upon mold portion 80 and the countermold portion 80' for securing these portions 80, 80' together to form an endorsed cavity. The recesses 81–85 of the mold portion 80 and recesses in the countermold portion 80' can be substantially symmetrical, however they need not necessarily be symmetrical as long as the properly shaped internal cavity is defined for injection molding the tissue repair device when the mold 80 and countermold 80' portions are brought together.

Tracks or recesses or first and second portions 84 and 85, respectively, in mold portion 80 (and the corresponding tracks or recesses in countermold portion 80') are each shaped to define anchoring members 14 with barbs 18 thereon. In this regard, recess or first channel 89 interconnecting recesses 84 and 85 is positioned in mold portion 80 as shown in FIG. 8 to receive flexible material 16 for linking anchoring members 14 together. Flexible material 16 is retained in place in mold portion 80 between projecting pegs 86 and 87 as shown in FIG. 9. Tracks or recesses 81, 82 and 83 serve as inlet channels for injection of fluid material under pressure into recesses 84 and 85 when the mold portion 80 and countermold portion 80' are closed.

The insert molding process of the present invention can be utilized to prepare the tissue repair devices illustrated in FIGS. 1–3, 4 and 7 of the present application and also the surgical clip device of U.S. Pat. No. 5,002,562 issued Mar. 26, 1991, the contents of which are incorporated by reference herein. In this regard, anchoring members 14 are formed of moldable material that can be subjected to injection molding, i.e. thermoplastic material which is rendered flowable upon requisite application of heat and/or pressure so that such material will flow into and fill the mold cavity taking the shape thereof, and then solidify upon cooling. Any of the suitable bioresorbable materials enumerated supra are capable of being injection molded into the requisite anchoring members 14. However, there is no requirement that the material used to form anchoring members 14 must be bioresorbable as long as such material is biocompatible and capable of being molded.

The bioabsorbable polymers which can be compression and/or injection molded include those derived from polyglycolic acid, glycolide, lactic acid, lactide, dioxanone, e-caprolactone, trimethylene carbonate, polyethylene oxide, etc., and various combinations of these and related monomers. Polymers of this type are known in the art, principally as materials for the fabrication of such surgical devices as sutures, wound clips, and the like, as disclosed, e.g., in U.S. Pat. Nos. 2,668,162; 2,703,316; 2,758,987; 3,225,766; 3,297,033; 3,422,181; 3,531,561; 3,565,077; 3,565,869; 3,620,218; 3,626,948; 3,636,956; 3,736,646; 3,772,420; 3,773,919; 3,792,010; 3,797,499; 3,839,297; 3,867,190; 3,878,284; 3,982,543; 4,047,533; 4,060,089; 4,137,921; 4,157,437; 4,234,775; 4,237,920; 4,300,565; and 4,523,591; U.K. Patent No. 779,291; D. K. Gliding et al., "Biodegradable polymers for use in surgery—polyglycolic/poly(lactic acid) homo- and co-polymers: 1", Polymer, Volume 20, pages 1459–1464 (1979), and D. F. Williams (ed.), *Biocompatibility of Clinical Implant Materials*, Vol. II, ch. 9: "Biodegradable Polymers" (1981). Copolymers of glycolide and lactide with or without additional monomers are preferred and of these glycolide-lactide copolymers are most preferred, for example a mixture of 80% by weight a 25/75 mole ratio Glycolide/Lactide copolymer blended with 20% by weight glycolide.

Material forming linking member 16 coupling the anchoring members 14 has flexibility greater than the material forming anchoring members 14. In this regard, the linking member 16 can be fabricated from the same bioresorbable materials supra and/or nonresorbable materials infra for fabricating the anchoring members 14. Flexibility is imparted to linking member 16 by providing the linking member 16 in fiber or filamentous form such as a suture. As used herein the term "fiber" or "filamentous" refers to materials which may be characterized as having a denier (see, e.g., *Plastics Terms Glossary, Fourth Edition*, Phillips Chemical Company, Bartlesville, Okla.).

Fiber-forming materials which are relatively inelastic are suitable for providing the linking member 16 provided such materials are more flexible than the anchoring members 14 and fairly rapidly bioabsorbed by the body, e.g., exhibiting a loss of tensile strength in from about 2 to about 26 weeks and total absorption within from about two to about fifty two weeks. It is to be understood, however, that the expression "relatively inelastic" does not preclude the presence of some minor degree of elasticity.

The linking member 16 can be composed of fibers or filaments of bioresorbable or nonresorbable material or from a blend of filaments possessing different bioabsorbabilities and elasticities to create a member 16 that is semi-absorbable. For example, linking member 16 can be fabricated from the composite yarn described in U.S. Pat. No. 4,990,158 issued Feb. 5, 1991 and the connective tissue prosthesis described in U.S. Pat. No. 5,147,400 issued Sep. 15, 1992, the contents of these United States patents being incorporated by reference herein.

The present invention may also be practiced with non-bioabsorbable absorbable polymeric materials having thermoplastic properties such as nylon, polyester, polypropylene, polytetrafluoroethylene (PTFE), polyethylene terephthalate (Dacron), etc. Non-absorbable materials which are especially suitable for fabricating the anchoring member or linking member of the invention device include silk, polyamides, polyesters such as polyethylene terephthalate, polyacrylonitrile, polyethylene, polypropylene, silk, cotton, linen, etc. Carbon fibers, steel fibers and other biologically acceptable inorganic fibroid materials can also be employed.

The term "non-bioabsorbable" as used herein applies to materials which permanently remain within the body or at least remain in the body for a relatively long period of time, e.g., at least about two years. It is preferred to employ a material which is also elastic, i.e., a polymeric material which in filamentous form exhibits a relatively high degree of reversible extensibility, e.g., an elongation at break of at least about 30 percent, preferably at least about 40 percent and more preferably at least about 50 percent. Fiber-forming polymers which are both non-bioabsorbable and elastic, and as such preferred for use herein, include fiber-forming polyolefins such as polyethylene homopolymers, polypropylene homopolymers, ethylene propylene copolymers, ethylene propylene terpolymers, etc., fluorinated hydrocarbons, fluorosilicones, isobutylenes, isoprenes, polyacrylates, polybutadienes, polyurethanes, polyether-polyester copolymers, and the like. Hytrel (DuPont), a family of copolyester elastomers based on (soft) polyether segments and (hard) polyester segments, and spandex, an elastomeric segmented polyurethane, provide especially good results.

Hytrel is manufactured in various commercial grades by DuPont, such as Hytrel 4056, 5526, 5556 and 7246. Hyrel 5556 is especially suitable when used to form a vascular graft, while Hytrel 7246 is well-suited when used to form a ligament prosthesis or tendon augmentation device.

Several properties of the various Hytrel grades are presented in the table below:

| | Hytrel Grade No. (Injection Molded at 23° C. for Testing) | | | |
|---|---|---|---|---|
| | 4056 | 5526 | 5556 | 7246 |
| Hardness in durometer points (ASTM Test No. D2240 Flexural Modulus (ASTM Test No. D790) | 40 | 55 | 55 | 72 |
| at −40° C. in MPa | 155 | 930 | 930 | 2,410 |
| at −40° F. in psi | 22,500 | 135,000 | 135,000 | 350,000 |
| at 23° C. in MPa | 55 | 207 | 207 | 518 |
| at 73° F. in psi | 8,000 | 30,000 | 30,000 | 75,000 |
| at 100° C. in MPa | 27 | 110 | 110 | 207 |
| at 212° F. in psi | 3,900 | 16,000 | 16,000 | 30,000 |
| ASTM Test No. D638 $^{(i)}$Tensile Strength at Break, | | | | |
| MPa | 28.0 | 40.0 | 40.0 | 45.8 |
| psi | 4050 | 5800 | 5800 | 6650 |
| $^{(i)}$Elongation at Break, % | 550 | 500 | 500 | 350 |
| $^{(ii)}$Tensile Stress at 5% Strain, | | | | |
| MPa | 2.4 | 6.9 | 6.9 | 14.0 |
| psi | 350 | 1,000 | 1,000 | 2,025 |
| $^{(ii)}$Tensile Stress at 10% Strain, | | | | |
| MPa | 3.6 | 10.3 | 10.3 | 20.0 |
| psi | 525 | 1,500 | 1,500 | 2,900 |
| Izod Impact (Notched) (ASTM Test No. D256, Method A) | | | | |
| at −40° C. in J/cm | No Break | No Break | No Break | 0.4 |
| at −40° F. in ft-lbf/in | No Break | No Break | No Break | 0.8 |
| at 23° C. in J/cm | No Break | No Break | No Break | 2.1 |
| At 73° F. in ft-lbf/in. | No Break | No Break | No Break | 3.9 |
| Resistance to Flex Cut Growth, Ross (Pierced), in Cycles to 100% cut growth (ASTM. Test No. D1052) $^{(iii)}$Initial Tear Resistance, Die C (ASTM Test No. D1004), | >1 × 10$^6$ | >5 × 10$^5$ | >5 × 10$^5$ | — |
| in kN/m | 101 | 158 | 158 | 200 |
| in lbf/in. | 580 | 900 | 900 | 1,146 |
| Melt Flow Rate in g/10 min. (ASTM Test No. D1238) Test conditions: | 5.3 | 18 | 7.0 | 12.5 |
| Temperature, ° C./Load, Kg $^{(iv)}$Melting Point (ASTM Test No. D3418) | 190/2.16 | 220/2.16 | 220/2.16 | 240/2.16 |
| in ° C. | 148 | 202 | 202 | 219 |
| in ° F. | 298 | 396 | 396 | 426 |
| Vicat Softening Point (ASTM Test No. D1525) | | | | |
| in ° C. | 108 | 180 | 180 | 207 |
| in ° F. | 226 | 356 | 356 | 405 |
| Specific Gravity (ASTM Test No. D792) | 1.16 | 1.20 | 1.20 | 1.25 |
| Water Absorption, 24 hr. in % (ASTM Test No. D570) | 0.6 | 0.5 | 0.5 | 0.3 |

$^{(i)}$head speed 50 mm/min. or 2 in./min.
$^{(ii)}$head speed 25 mm/min. or 1 in/min.
$^{(iii)}$specimens 1.9 mm or 0.075 in. thick.
$^{(iv)}$differential scanning calorimeter (DSC), peak of endotherm Corresponding properties of other grades of Hytrel are available from DuPont.

The fibers or filaments forming the linking member can be woven, braided or knitted in whole or in part and will ordinarily possess a relatively high tensile strength, e.g., a straight tensile strength of at least about 30,000 p.s.i., preferably at least about 60,000 p.s.i. and more preferably at least about 90,000 p.s.i.

Bioabsorbable polymers of high lactide or glycolide content, e.g., those in which at least about 75 percent of the monomeric units are derived from either glycolide or lactide, are preferred for the construction of the linking member 16 of tissue repair device. Typical polymers are disclosed in U.S. Pat. Nos. 4,523,591 and 4,744,365 which are incorporated by reference. Polymers of high glycolide content tend to be absorbed more quickly than those possessing a high lactide content. Accordingly, the glycolide-based polymers may be preferred, e.g., for both the anchoring members 14 and even the linking member 16. An especially preferred lactide-glycolide copolymer for forming the linking member 16 contains from about 70 to about 90 percent, and preferably from about 75 to about 85 mole percent lactide monomer with the balance being provided by the glycolide monomer. Thus, for example, fibers or filaments formed from a lactide-glycolide copolymer based on 80 mole percent lactide-20 mole percent glycolide is especially advantageous for constructing the linking member 16, and ultimately, the tissue repair device of the present invention. When a composite yarn is used to form the linking member 16, then the sheath yarn component, which is preferably braided around the core yarn component, may comprise a plurality of bioabsorbable fibers in turn comprising at least two different chemical compositions. This copolymer is also suitable for injection molding anchoring members 14 about linking member 16.

As pointed out supra, the various fibers or filaments can be woven, braided or knitted together to form linking member 16. In this regard, the term "braid" or "braided" refers to an arrangement of discrete units or bundles, denominated "sheath yarns," made up of individual filaments with individual sheath yarns interlocking or interlacing each other in a regular criss-cross pattern. For example, a suitable braided suture which can be utilized as the linking member 16 is disclosed in U.S. Pat. No. 5,019,093 issued May 28, 1991 and U.S. Pat. No. 5,226,912 issued Jul. 13, 1993, the contents of which are incorporated by reference herein. Such braided yarn encompasses core and sheath designs as well as braid over braid designs. The core is optional and can be twisted, ply or cable.

In another embodiment, the fibers or filaments forming the linking member 16 are woven into a spiroid braid construction. The expressions "spiroid braid" and "spiroid braided" refer to various types of a solid arrangement of discrete units or bundles, denominated "yarns", made up of individual filaments or fibers. The yarns are arranged substantially parallel to the longitudinal axis of the suture or linking member 16 and internally engaging each other in a repetitive spiral pattern. The term "solid" is intended to designate a suture or linking member 16 in which the filamentous material of its construction occupies substantially the entire cross-sectional areas of the suture or linking member 16 with at most a minor percentage of such area (not exceeding about 25% in the larger suture sizes) constituting void spaces or interstices between adjacent yarns and fibers. Such construction contrasts with that of e.g., a standard suture which, in the absence of a core component, possesses a lumen representing a significant percentage of the cross-sectional area of the suture.

Spiroid braided suture component or linking member 16 can also be fabricated from a wide variety of natural and synthetic fibrous materials such as any of those heretofore disclosed for the construction of sutures. Such materials include non-absorbable as well as partially and fully bioabsorbable (i.e., resorbable) natural and synthetic fiber-forming polymers. Examples of spiroid braid constructions which can be utilized as the linking member 16 in the tissue repair device of the present invention are found in U.S. Pat. No. 5,133,738 issued Jul. 28, 1992 and 5,181,923 issued Jan. 26, 1993, the contents of which are incorporated by reference herein.

The present invention is especially suited for preparing the tissue repair device by injection molding which will be described infra with respect to FIGS. 8–10.

Initially, the mold is opened and the fiber or filament-like material forming the linking member 16 is positioned between projecting pegs 86 and 87 within first channel 89 as schematically illustrated in FIG. 9. The mold is then closed by fitting mold portion 80 and countermold portion 80' together in the direction of arrows A and B as shown in FIG. 10. After mold portion 80 and countermold portion 80' are secured together, the thermoplastic material forming the anchoring members 14 is heated to a temperature at which this material becomes flowable. In this regard, the thermoplastic material is preferably heated to a temperature from about 120 to about 240° C., more preferably from about 140 to about 200° C. The thermoplastic material is heated in a plunger machine (not illustrated) remote from the mold portions, an example of which is shown in the *Encyclopedia of Polymer Sciences and Engineering* citation noted supra.

The mold portion 80 is provided with proximal ends 180, sidewalls 182 and pointed distal ends 184. Likewise the countermold 80' is provided with such structure. Next, the molten thermoplastic material is injected, under pressure, into the mold cavity defined by recesses or channels 81–85 of mold portion 80 and corresponding recesses or channels 81'–85' of countermold portion 80'. The molten material is injected into the mold cavity through opening 88–88' defined by mold 80 and countermold 80' portions into inlet channel 81. Injection is carried out from the (non-illustrated) plunger apparatus which is preferably an extruder screw having a nozzle or an end thereof extending into opening 88–88' during injection. In this regard, the molten thermoplastic material is preferably injected at a pressure of about 400 to about 4,000 psi, more preferably about 500 to about 2,000 psi.

During the injection, the mold/countermold portions are preferably at about room temperature (about 20° C.) so that the injected thermoplastic material will ultimately cool to form the hardened anchoring members 14 about the linking member 16. In this regard, the mold/countermold portions 80 and 80' can be desirably heated to enhance smooth flowing of the thermoplastic material along recesses or channels 81–85 and 81'–85'. The mold portions can be preferably heated to a temperature up to about 50° C., more preferably up to about 40° C. However, the mold portions 80 and 80' will ultimately have cool to room temperature in order to ensure hardening of the thermoplastic material into anchoring members 14. The channels are formed in mold 80 and countermold 80' portions such that thermoplastic material will not flow into the cavity or first channel defined by recesses 89 and 89', i.e. the channel defining the linking member 16. Accordingly, when the molten thermoplastic material is injected into the mold portions 80 and 80', the material will be unable to flow into channels 89 and 89' and will not cover the filamentous or fiber material forming linking member 16 at this point. As a result, flexibility of linking member 16 will be maintained even after anchoring members 14 have hardened upon cooling of the thermoplastic material forming the same.

Injection is carried out until the cavity defined by channels 81–85 and 81'–85' is completely filled with thermoplastic material, i.e. the thermoplastic material can no longer flow into the mold cavity through opening 88–88'. After injection is completed, the thermoplastic material is allowed to cool and set within the mold cavity to form anchoring members 14. Preferably, the thermoplastic material is allowed to cool and set after injection is completed for about 0 to about 1 minute, more preferably from about 1 to about 8 seconds.

Figure 11:
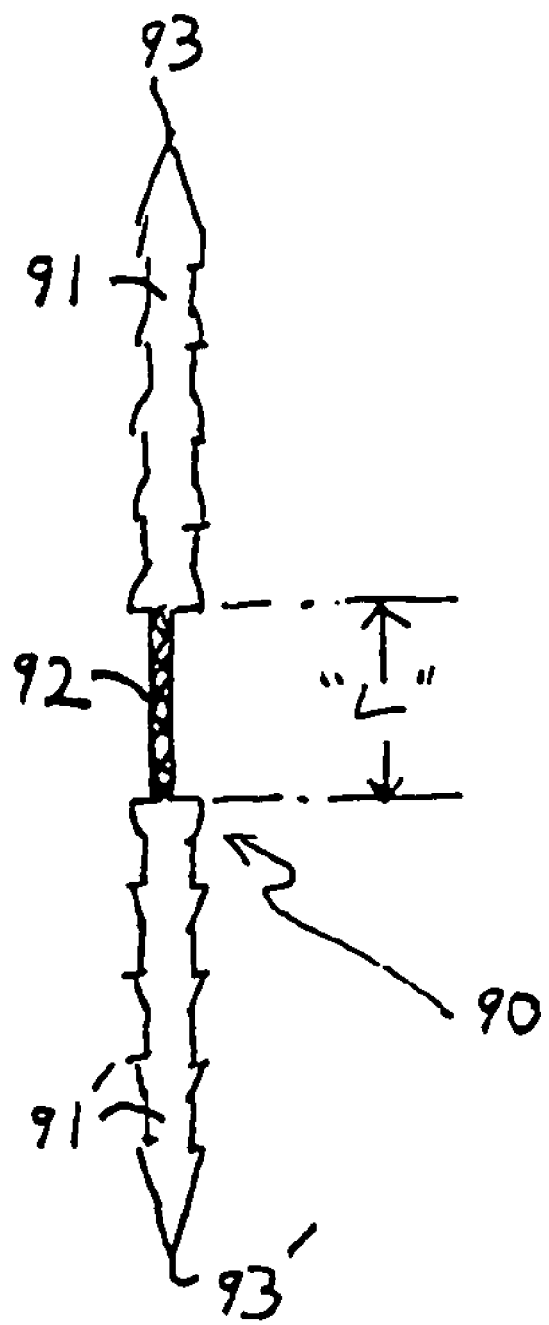
FIG. 11 is a side view of the device fabricated with the apparatus of FIGS. 8–10.

After the injected thermoplastic material has sufficiently cooled and solidified, then the mold and countermold portions 80 and 80' are opened and the molded part contained therein removed from mold portion 80. The gates formed on anchoring members 14 (where channels 84 and 85 respectively meet channels 82 and 83 in mold portion 80) are cut, preferably by means of a manual or powered cutting tool, so that anchoring members 14 are separated from the thermoplastic material that has solidified along channels 81–83. The resulting product 90 is shown in FIG. 11 and comprises anchoring members 91, 91' secured to flexible material 92 forming the linking member. The tips 93, 93' of respective anchoring members 91, 91' can then be secured to appropriate needles, e.g., by adhesives, crimping, swaging, etc.

The mold and countermold portions 80 and 80' along with the molding cavity formed therebetween can have any suitable dimensions required for molding a suture repair device. For example, the length of the entire product shown in FIG. 11 (from tip 91 to tip 91') is preferably about 0.120 to about 6 inches with the corresponding length of each anchoring, member 91, 91' about 0.040 to about 2 inches, leaving an exposed area of filament-like flexible material 92 of about 0.040 to about 2 inches in length. Dimensions of the molding cavity formed by tracks or recesses 81–85, 89 and 81'–85', 89' can be accordingly prepared to mold the product 90 possessing these dimensions. The length of material 92 cut and positioned within tracks or recesses 84, 85 and 89 as shown in FIGS. 9 and 10 will naturally vary depending upon the appropriate dimensions of these tracks.

As noted supra, the structure of flexible material 16 which is preferably filamentous or fiber-like, can be woven, braided or knitted, e.g., take the form of a tubular or solid spiroid braid. The material forming the linking member 92 can be different from, or even the same as the material used to form anchoring members 91, 91' shown in FIG. 11. In other words, linking member 92 and anchoring members 91, 91' can be formed from the same material which possesses greater flexibility in a filament or fiber-like condition (linking member 92) than when present as a solidified mass of previously molten thermoplastic material (anchoring members 91, 91').

However, preferably the linking member 92 (FIG. 11) is constructed out of material such that the portion of the braid that contacts the molten thermoplastic material will itself undergo a partial melting. The braid will then fuse to the molten material as the material cools and hardens, forming a strong secure bond between flexible linking member 92 and substantially rigid anchoring members 91, 91' which will not prematurely fail prior to and during insertion into tissue. Typically the length "L" of linking member 92 extending from anchoring member 91 to anchoring member 91' is in the range of about 1 mm to about 50 mm. Typically, length "L" is sufficient for anchoring members 91, 91' to be arranged parallel after solidification.

Figure 12:
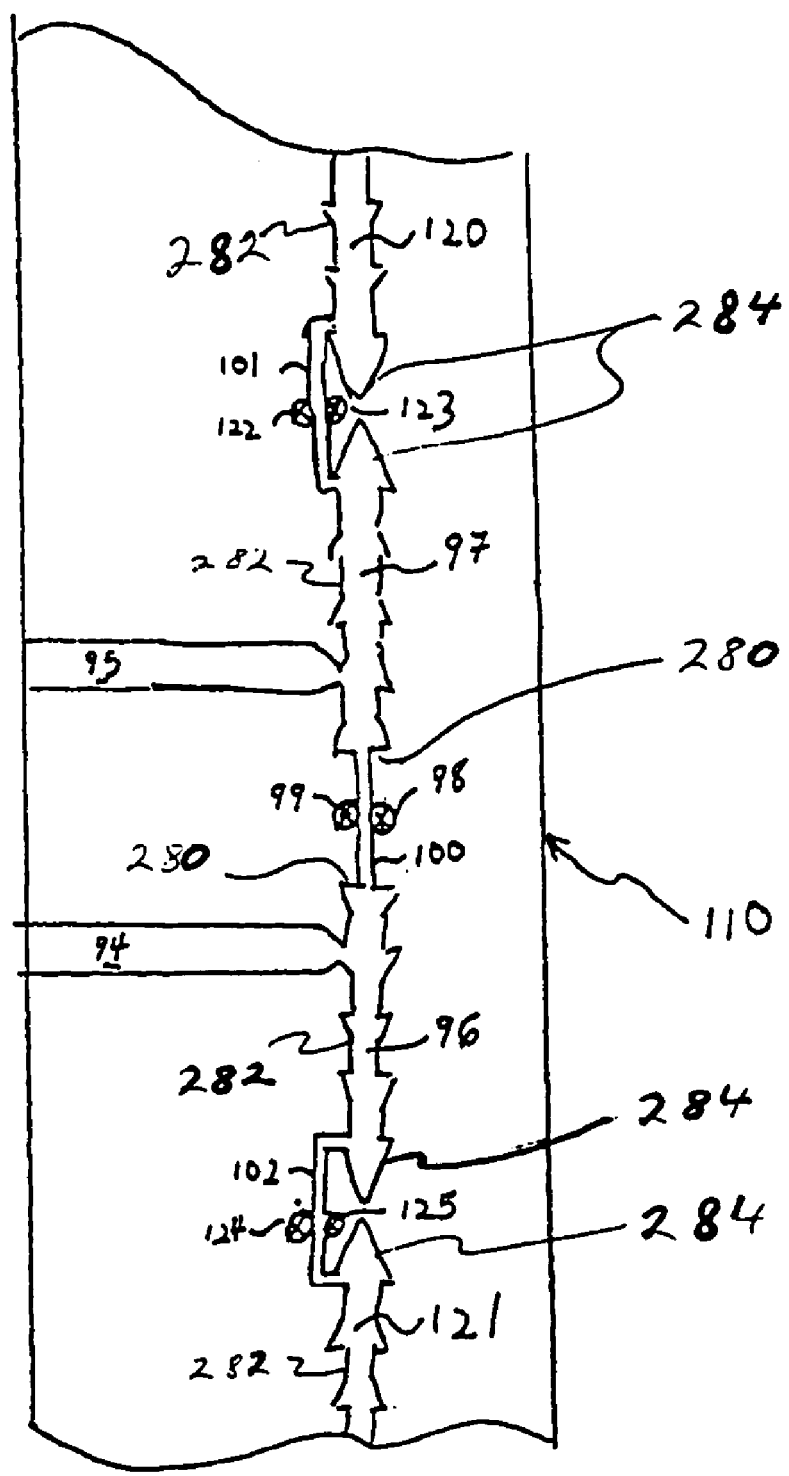
FIG. 12 is a broken top view of an alternative embodiment of apparatus used to fabricate the invention device.

It is possible to mold a series of tissue repair devices formed along single, extending strands or ligature of flexible material which can then be severed at appropriate locations to form multiple tissue repair devices. The molding procedure to form a series of these devices is the same as the molding procedure described supra, the only difference being that mold and countermold portions define a cavity for retaining a length of flexible material with appropriate recesses positioned therealong to mold several anchoring members along the length of the flexible material. An example of such a mold portion 110 is shown in FIG. 12 which is a partial view of the same. The mold portion 110 is provided with proximal ends 280, sidewalls 282 and sharp pointed distal ends 284. As can be seen in this view, the tracks or recesses 94–97 defining the flow of molten thermoplastic material are substantially identical to tracks or recesses 82–85 in the mold portion 80 shown in FIGS. 8–10. Additionally, tracks or recesses 100, 101 and 102 are provided for retaining a length of flexible material 16 between the respective tracks or recesses 96, 97, etc. for molding anchoring members. Tracks 101 and 102 are offset from respective recesses 120/97 and 96/121 as illustrated in FIG. 12. Respective projecting pegs 122/123 and 124/125 are also provided on either side of tracks 101 and 102. The countermold portion for this mold apparatus also comprises tracks and recesses forming the exact mirror image of tracks 94–97, 100–102, 120–121, etc. of mold portion 110 with the exception of recesses being provided to received projecting pegs 98, 99, 122, 123, 124 and 125 when the mold and countermold portions are secured to one another.

Figure 13:
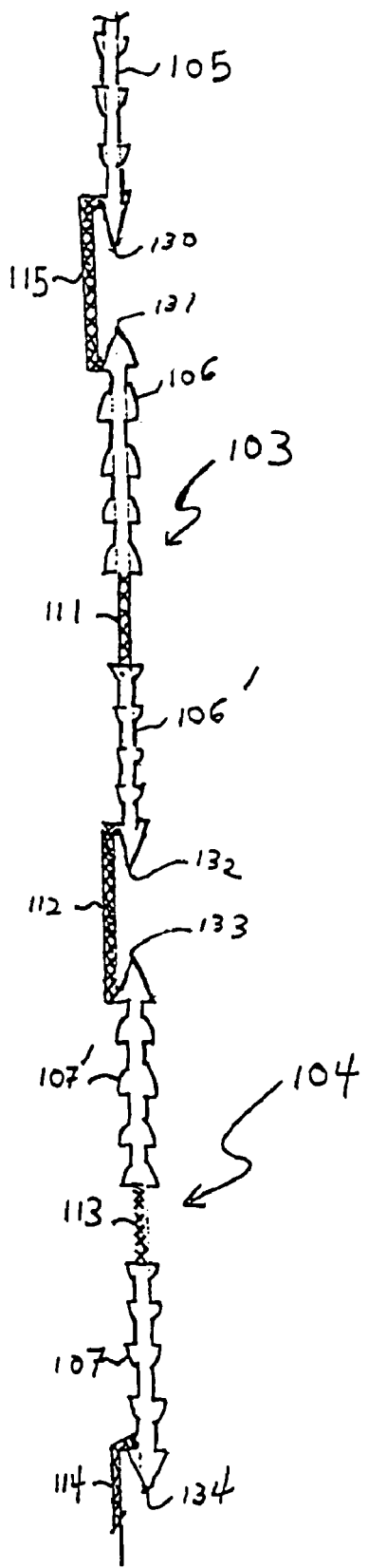
FIG. 13 is a broken side view of the invention device fabricated with the apparatus illustrated in FIG. 12.

An example of the product prepared with the mold of FIG. 12 is shown in FIG. 13 (after removal of the gates therefrom) where a series of tissue repair devices 103, 104, 105 (in part) are illustrated with respective anchoring members 106, 106', 107, 107', 108, 108' (not illustrated) molded about the flexible material having exposed sections 111, 112, 113, 114, 115. The mold tracks 101 and 102 have been positioned in the mold portion of FIG. 12 such that the exposed sections of flexible material 115, 112, 114 positioned therein are offset form the tips 130–134 of the respective anchoring members. It is particularly preferred not to have the flexible material pass through the points of tips 130–134. This preserves the sharpness of the points of the respective anchoring members. After injection molding has been completed and the resulting repair device series removed from the mold with the gates being severed, then the flexible material is cut at the appropriate locations, i.e., at exposed sections 109, 112, 114 to form the individual tissue repair devices 103, 104 and 105. Anchoring members 106, 106', 107, 107', 105, 105' can then be attached to appropriate needles by the methods described supra or left alone.

Figure 14:
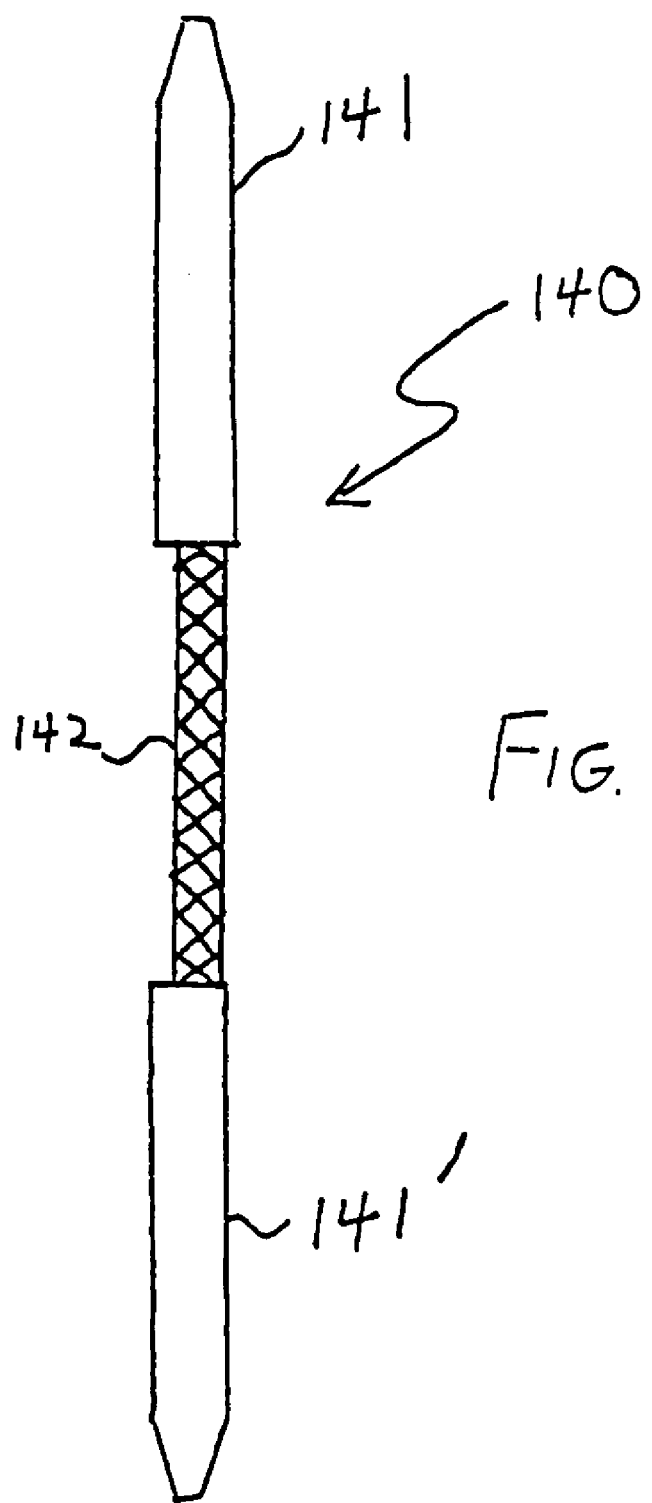
FIG. 14 is a top plan view of an alternative embodiment of a tissue repair device fabricated in accordance with the present invention.

The tracks or recesses formed within the mold cavity can take any convenient size or shape to ultimately form a tissue repair device having any suitable dimensions or shapes. For example, the mold cavity can be configured to mold a tissue repair device 140 illustrated in FIG. 14 where unlike the devices illustrated in FIGS. 11 and 13, the anchoring members 141, 141' do not possess barbs (reference numeral 142 denotes the linking member).

Figure 15:
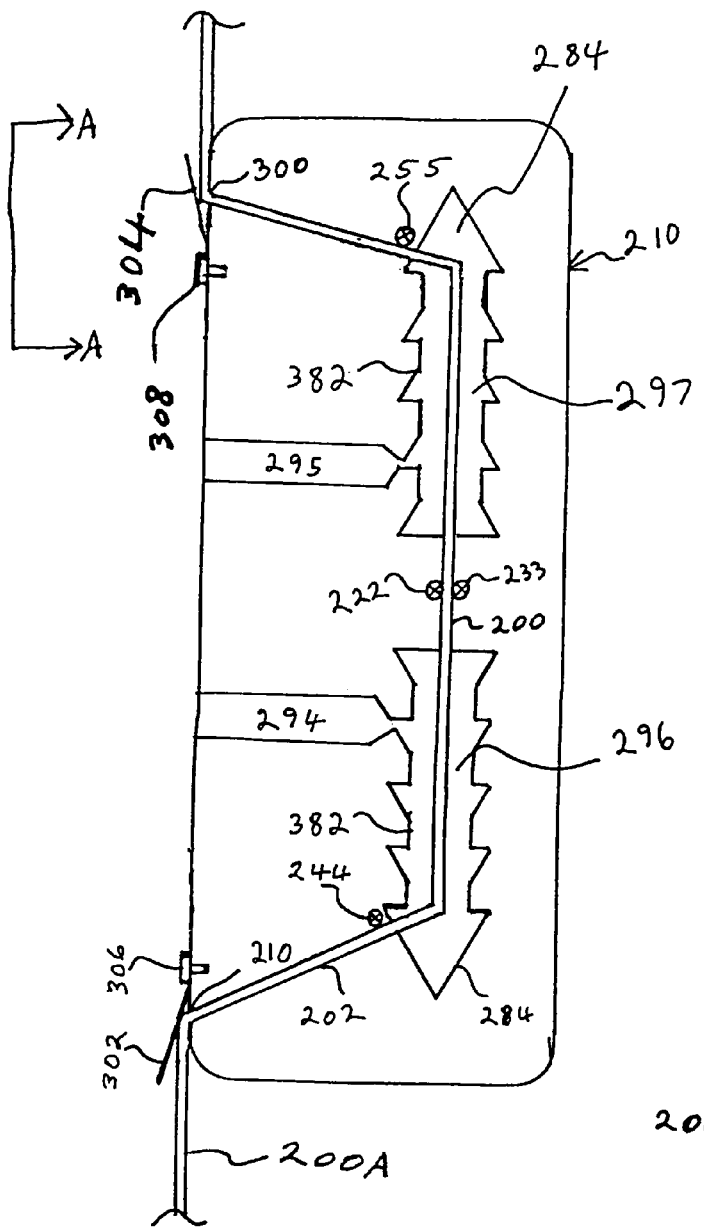
FIG. 15 is a top view of an alternative embodiment of apparatus used to fabricated the invention device.
Figure 16:
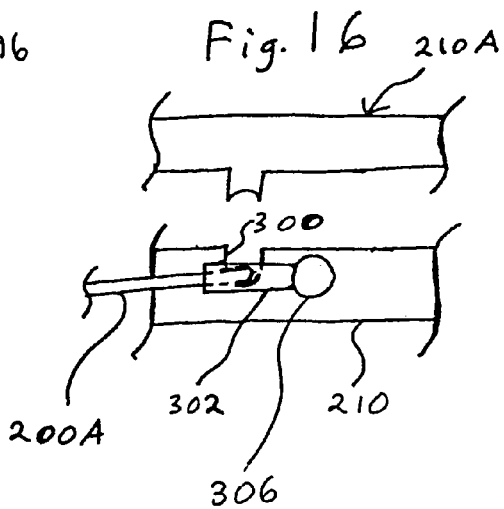
FIG. 16 is a side view of a portion of the apparatus of FIG. 16 and its countermold in the direction of arrows A—A in FIG. 15.

FIG. 15 shows additional details of a mold 210 employed with the present invention. A length of flexible material 200A enters the mold at entry port 210, passes along a track 202, past a peg 244 and into a recess 296. Recesses 296 and 297 communicate with tracks 294, 295 to provide a path for molten polymer. Flexible material 200A passes from the recess 296 along a channel 200 between pegs 222 and 233 and into and out of recess 297 as illustrated in FIG. 15. Then, the material 200A passes along a channel 201 past a peg 255 and exits the mold 210 at exit port 300. Leaf springs 302, 304 are respectively located at the entry port 210 and exit port 300 and are attached to the mold 210 by respective bolts 306 and 308. FIG. 16 illustrates an enlarged view of a portion of the mold 210 in the direction of arrows A—A in FIG. 15 in addition to a portion of countermold 210A mating with mold 210.

The following examples are illustrative of the fabrication of a tissue repair device in accordance with the present invention.

EXAMPLE 1

A length of about 0.25 inches of spiroid braided flexible material formed of a copolymer of glycolide and lactide of approximately 18 mol % glycolide and 82 mol % lactide is cut and placed in mold portion 80 as shown in FIG. 9 in the channel 89 between projecting pegs 86 and 87. The mold 80 and countermold 80' portions (FIG. 10) are then secured together. Then, material of the same composition is separately heated to a temperature of about 150° C. so that the material melts and is in flowable condition. Next, this molten flowable material is injected into the mold cavity under a pressure of about 2,000 psi., until the mold cavity is completely filled with the molten, thermoplastic material, i.e., the material can no longer flow into the mold cavity. The mold cavity itself, i.e. mold parts 80 and 80', are at a temperature of about 15° C.

After filling of the mold cavity with the thermoplastic material is completed, the mold portions 80 and 80' are allowed to cool to room temperature over a period of about 2 seconds, at which time the thermoplastic material has solidified into fairly rigid members 91, 91'. The mold cavity is opened and the gates attaching members 91, 91' to the solidified material in tracks 82 and 83 are cut, resulting in the tissue repair device illustrated in FIG. 11 and which is then attached to needles at points 93, 93' thereof.

The above procedure is also carried out with tubular braided material of the same composition to form linking member 92.

EXAMPLE 2

The procedure of Example 1 supra is repeated in its entirety but with about 4–6 inches of a U.S.P. size 2-0 braided suture material composed of about 92.5 mol % glycolide and about 7.5 mol % lactide as the flexible material 92 and a copolymer of about 92.5 mol % glycolide and about 7.5 mol % lactide as the molten thermoplastic material hardening to form rigid members 91, 91'.

While the invention has been particularly shown and described with reference to the preferred embodiments, it will be understood by those skilled in the art that various modifications and changes in form and detail may be made therein without departing from the scope and spirit of the invention.

Accordingly, modifications such as those suggested above, but not limited thereto, are to be considered within the scope of the invention.

What is claimed is:

1. Method for fabricating a composite device of two components possessing different flexibilities, comprising the steps of:
    placing a first component which is in woven, braided or knitted form in a mold cavity of a mold;
    heating thermoplastic material forming a second less flexible component to a temperature sufficient to melt the material and render the same in flowable condition;
    introducing the molten material into the mold cavity until the molten material fills the cavity and surrounds an outer portion of the first component previously placed in the cavity; and
    allowing the molten material in the cavity to cool and solidify to form a solid, substantially rigid component;
    whereby secure reliable attachment is formed between the first and second components having different flexibilities.

2. The method of claim 1, wherein the molten material is introduced under pressure in the mold cavity to effect a molding step selected from the group of injection molding and compression molding.

3. The method of claim 1, wherein the molten material flows into the mold cavity and solidifies therein to form two separate solid, substantially rigid components attached to the first component placed with the mold cavity.

4. The method of claim 3, wherein a tissue repair device is formed having a center portion of filamentous material secured to outer substantially rigid, solid portions and which serve to anchor said device in tissue when introduced into the same.

5. The method of claim 1, wherein both said components are formed from the same material.

6. The method of claim 3, wherein the first component has a length such that said rigid components are parallelly arrangable to each other.

7. The method of claim 1, wherein fibers of filaments of the first component form a solid spiroid braided structure.

8. The method of claim 1, wherein fibers or filaments of the first component from a tubular braid or braided sheath over a braided core structure.

9. The method of claim 1, wherein the thermoplastic material is heated to a temperature of about 120 to about 240° C.

10. The method of claim 1, wherein the thermoplastic material is injected into the mold cavity at a pressure of about 400 to about 4,000 psi.

11. The method of claim 9, wherein the mold cavity is at a temperature of about 20 to about 50° C. during injection.

12. The method of claim 1, wherein the mold cavity is allowed to cool for about 0 to about 1 minute after introduction of the molten thermoplastic material has been completed.

13. The method of claim 1, wherein both components are formed from bioabsorbable material.

14. The method of claim 13, wherein the first component placed in the mold cavity is formed from material derived from the group consisting of polyglycolic acid, glycolide, lactic acid, lactide, dioxanone, e-caprolactone, trimethylene carbonate, polyethylene oxide and mixtures thereof.

15. The method of claim 14, wherein the material is a copolymer of glycolide-lactide.

16. The method of claim 1, wherein the thermoplastic material is selected from the group consisting of polyethylene homopolymers, polypropylene homopolymers, ethylene propylene copolymers, ethylene propylene terpolymers, fluorinated hydrocarbons, fluorosilicones, isobutylenes, isoprenes, polyacrylates, polybutadienes, polyurethanes, polyetherpolyester copolymers and mixtures thereof.

17. The method of claim 1, wherein the mold cavity has a pointed distal end, a proximal end and two side walls, the first component is placed in the mold cavity such that it passes through a side wall of the cavity and a proximal end of the cavity, thereby the first component does not pass through said pointed distal end.

18. The method of claim 4, wherein said substantially rigid components comprise first and second substantially rigid components, each substantially rigid component respectively comprising a first and a second blunt end, a first and a second pointed end, and first and second sidewalls;
    said filamentous material enters said mold, passes through said first sidewall and first blunt to said second blunt end, through said second blunt end and second sidewall and exits from said second sidewall;
    further comprising the step of applying tension to said filamentous material where it enters and exits the mold.

19. The method of claim 18, wherein leaf springs attached to said mold tension said filamentous material.

20. The method of claim 19, further comprising the step of holding said filamentous material between a pair of rigid members within said mold between said first and second substantially rigid members.

21. Apparatus for fabricating a composite device of first and second components possessing different flexibilities, comprising:
    a mold comprising a mold cavity including an inlet channel, a first portion, a second portion and a first channel extending between the first and second portions, the inlet channel communicating with the first and second portions and being spaced from the first channel, such that the molten material must flow from the inlet channel through the first portion or second portion before communicating with the first channel, the first channel being dimensioned to receive a first component of greater flexibility than the second component, the first component being in woven, braided or knitted form and dimensioned such that molten material is prevented from entering the first channel when the first component is received in the first channel;
    means for heating thermoplastic material forming a second less flexible component to a temperature sufficient to melt the material and render the same in flowable condition;
    means for introducing the molten material into the mold cavity until the molten material fills the cavity and surrounds a portion of the first component previously placed in the cavity; and
    means for allowing the molten material in the cavity to cool and solidify to form a solid, substantially rigid component;
    whereby secure reliable attachment is formed between two components having different flexibilities.

22. Apparatus of claim 21, wherein said first portion and said second portion respectively are adapted for defining first and second substantially rigid components;
    each substantially rigid component having a respective pointed end, blunt end and sidewalls;
    a second channel in communication with the surface of said mold and said first cavity portion sidewalls;
    the first channel being in communication with said first and second cavity portions at locations defining said blunt ends; and a third channel communicating with said second cavity and said mold surface; and further comprising means for tensioning said first component of greater flexibility, said tensioning means attached to said mold.

23. Apparatus of claim 22, wherein said tensioning means comprise leaf springs for contacting said first component of greater flexibility.

24. Apparatus of claims 23, further comprising:

means for positioning said first component of greater flexibility within said second channel.

25. Apparatus of claim 24, wherein said positioning means comprise a first peg along a first side of said second channel and a second peg along a second side of said second channel.

26. Apparatus of claim 21, wherein the first channel is dimensioned to receive the first component such that the flow of molten material from the first and/or second cavity portions into the first channel is substantially prevented.

* * * * *